(12) United States Patent
Flower

(10) Patent No.: US 6,208,891 B1
(45) Date of Patent: Mar. 27, 2001

(54) DISABLING CIRCUIT FOR AN IONTOPHORETIC SYSTEM

(75) Inventor: Ronald J. Flower, Vernon, NJ (US)

(73) Assignee: Drug Delivery Technologies, Inc., New York, NY (US)

( * ) Notice: Subject to any disclaimer, the term of this patent is extended or adjusted under 35 U.S.C. 154(b) by 0 days.

(21) Appl. No.: 08/835,153

(22) Filed: Apr. 4, 1997

(51) Int. Cl.[7] .................................................. A61N 1/30
(52) U.S. Cl. ............................................. 604/20; 607/62
(58) Field of Search .............................. 604/20.21, 501, 604/503; 607/149, 152, 62–64

(56) References Cited

U.S. PATENT DOCUMENTS 5,697,896 * 12/1997 McNichols et al. .

* cited by examiner

Primary Examiner—Mark Bockelman
(74) Attorney, Agent, or Firm—Kirkpatrick & Lockhart LLP

(57) ABSTRACT

An apparatus and a corresponding method for the iontophoretic delivery of drugs that operates only when the supply voltage is higher than a predetermined threshold is provided. The apparatus includes a current control circuit for controlling the current in an iontophoretic patch, and a supply voltage detection circuit. When a low supply voltage is detected, the current control circuit is disabled, which stops the iontophoretic current, thereby stopping the delivery of drugs.

13 Claims, 3 Drawing Sheets

DISABLING CIRCUIT FOR AN IONTOPHORETIC SYSTEM

BACKGROUND OF THE INVENTION

1. Field of the Invention

The invention is in the field of iontophoresis. In particular, the invention relates to disabling automatically an iontophoretic drug delivery device when the device supply voltage falls below a certain level, thereby preventing any further delivery of drugs to the patient under a condition that may compromise the proper operation of the device.

2. Description of the Related Art

Iontophoresis is the application of an electrical current to transport ions through intact skin. One particularly advantageous application of iontophoresis is the non-invasive transdermal delivery of ionized drugs or other therapeutic agents into a patient. This is done by applying low levels of current to a patch placed on the patient's skin, which forces the ionized drugs contained in the patch through the patient's skin and into his or her bloodstream.

Passive transdermal patches, such as those used to deliver nitroglycerin for angina pectoris, estradiol for hormone replacement, and nicotine to stop smoking, can only use a limited number of drugs because they work by diffusion. Iontophoresis advantageously expands the range of drugs available for transdermal delivery, including, for example, parenteral drugs (e.g., peptides). Further, because the amount of drug delivered is related to the amount of current applied, the drug delivery rate can be precisely controlled by controlling the current, unlike the passive transdermal patches. This allows for more rapid delivery (onset) and drug reduction (offset) in the patient.

When compared to drug delivery by needle injection, iontophoresis can have less physical and emotional trauma, pain, and possibility of infection. Transdermal drug delivery by iontophoresis also avoids the risks and inconvenience of IV (intravenous) delivery. In addition, when compared to oral ingestion of drugs, drug delivery by iontophoresis bypasses the GI tract, thus reducing side-effects such as drug loss, indigestion and stomach distress, and eliminating the need for swallowing the drug. Iontophoresis also avoids drug loss due to hepatic first pass metabolism by the liver that occurs when drugs are ingested.

Further, transdermal drug delivery by iontophoresis permits continuous delivery of drugs with a short half life and easy termination of drug delivery. Because iontophoresis is more convenient, there is a greater likelihood of patient compliance in taking the drug. Thus, for all of the above reasons, iontophoresis offers an alternative and effective method of drug delivery, and an especially useful method for children, the bedridden and the elderly.

An iontophoretic drug delivery system typically includes a current source, such as a battery and current controller, and a patch. The patch includes an active reservoir and a return reservoir. The active reservoir contains the ionized drug, for example, in a conductive gel. The return reservoir contains a saline gel and collects ions emanating from the patient's skin when the drug is being delivered into the patient's skin.

The patch also has two electrodes, each arranged inside the active and return reservoirs to be in respective contact with the drug and saline. The anode, or positive, electrode and the cathode, or negative, electrode are respectively electrically connected to the anode and cathode of the current source by electrical conductors. Either the anode electrode or the cathode electrode is placed within the drug reservoir, depending on the charge of the ionized drug. This electrode is designated as the active electrode. The other electrode is placed within the return reservoir, and is designated as the return electrode.

The active electrode has the same charge as the ionized drug to be delivered and the return electrode has a charge opposite of the drug to be delivered. For example, if the drug to be delivered to the patient has a positive ionic charge, then the anode will be the active electrode and the cathode will be the return electrode. Alternatively, if the drug to be delivered has a negative ionic charge, then the active electrode will be the cathode and the return electrode will be the anode. When current from the current source is supplied to the active electrode, the drug ions migrate from the drug gel in the reservoir toward and through the skin of a patient. At the same time, oppositely-charged ions flow from the patient's skin into the saline solution of the return reservoir. Charge is transferred into the return electrode and back to the current source, completing the iontophoretic circuit.

The electronic controller between the battery and the electrodes delivers the required current to the patch. The controller may control the output current so that drug delivery is accomplished at a constant or varying rate, or over a short, long or periodic time interval. These controllers generally require relatively complex electrical circuits, sometimes including microprocessors, to meet the above requirements.

Under ordinary operating conditions, the power supply voltage (e.g., the battery voltage) is above the minimum operating voltage of the device circuitry. In this situation, the operation of the device circuitry is predictable. If the battery voltage drops below the minimum operating voltage, however, operation of the device circuitry becomes unpredictable, and the device circuitry may not function properly.

The electronic controller may be programmed to shut off the current control circuit when a low voltage condition is detected. But this approach only works if the supply voltage is high enough for the controller to operate. If the supply voltage drops below this level, the shut off mechanism may not operate properly.

In particular, if the supply voltage drops below a certain level, and the operation of the components is unpredictable, the current control circuit may supply current to the patch, which would cause the drug to be delivered to the patient. In this malfunction condition, the iontophoretic current may even be higher than the current that is supplied when the supply voltage is correct. If this occurs, higher dosage of drugs could be delivered to the patient.

SUMMARY OF THE INVENTION

The present invention advantageously prevents any delivery of drugs to the patient when the power supply voltage falls below a certain level, by disabling the current control circuit upon the detection of this condition.

In one aspect of the invention, a fail-safe iontophoretic drug delivery apparatus is provided. This apparatus includes a voltage detection circuit and an iontophoretic current control circuit. The voltage detection circuit outputs a signal to the current control circuit when the supply voltage falls below a predetermined level, causing the current control circuit to stop supplying the iontophoretic current.

BRIEF DESCRIPTION OF THE DRAWINGS

These and other features and advantages of the present invention can be understood by reference to the detailed description of the preferred embodiments set forth below taken with the drawings, in which.

DETAILED DESCRIPTION OF THE PREFERRED EMBODIMENTS

Figure 1:
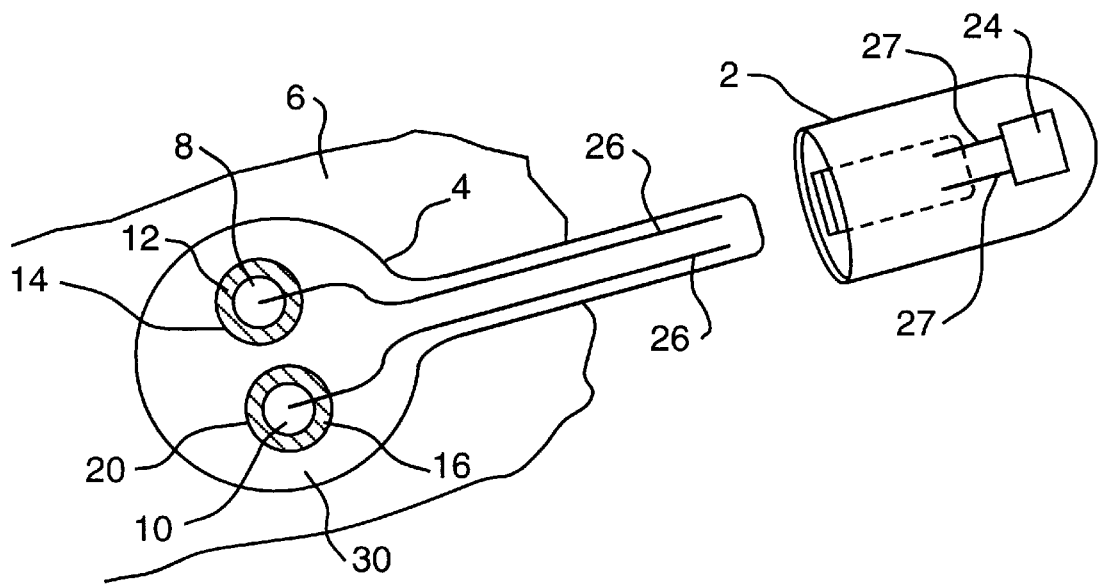
FIG. 1 is a perspective view of an iontophoretic drug delivery device.

One type of iontophoretic drug delivery device includes a separate, reusable controller 2, which can be removably and electrically connected to a patch 4 containing the drug, therapeutic agent or medicament, as shown in FIG. 1. The patch 4 is attached to the skin of the patient 6. The patch includes an active electrode 8 and a return electrode 10, with the ionic drug 12 and active electrode 8 positioned within the active reservoir 14, and the saline or electrolyte 16 and return electrode 10 positioned within the return reservoir 20.

Figure 2:
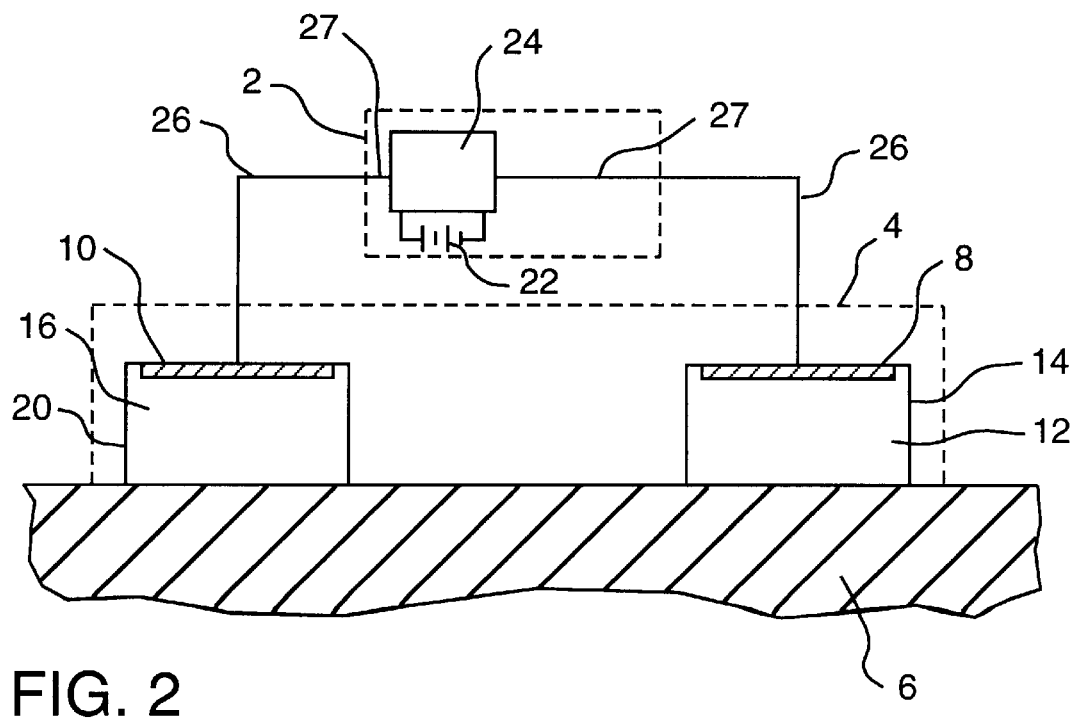
FIG. 2 is a high-level block diagram of an iontophoretic drug delivery device.

The iontophoretic drug delivery device also includes a controller 2 having a power supply 22 and electronic control circuitry 24, as shown in FIG. 2. The controller is electrically coupled to the patch 4 using electronic interconnectors 26, such as a printed flexible circuit, metal foils, wires, tabs or electrically conductive adhesives. The power supply 22 in combination with the electrodes 8 and 10 and the patient's body 6 completes the circuit and generates an electric field across the body surface or skin on which the iontophoretic device is applied. The electric field causes the drug in the active reservoir 14 to be delivered into the body of the patient by iontophoresis.

Patch 4 is generally a planar flexible member formed of, for example, a biocompatible material such as woven or non-woven textiles or polymers, or any other construction well-known in the art. The patch is attached to the patient's skin using adhesives or a strap or both. The patch includes an enlarged patch body 30, which includes the active and return reservoirs.

The lower surface of the reservoirs are placed in contact with the skin. The electrodes are positioned so that an electrical current path is established between the electrodes 8 and 10 through the reservoirs and the patient's skin 6. Electrodes 8 and 10 are placed in conductive contact with the reservoirs 12 and 16, respectively. A direct current source may be connected to the electrodes 8 and 10 so that the active electrode has the same charge polarity as the ionic drug. When current is passed through the active electrode 8 to the return electrode 10 through the skin 6, the ionic drug 12 contained in the active reservoir 14 is delivered through the skin 6 and into the patient.

Figure 3:
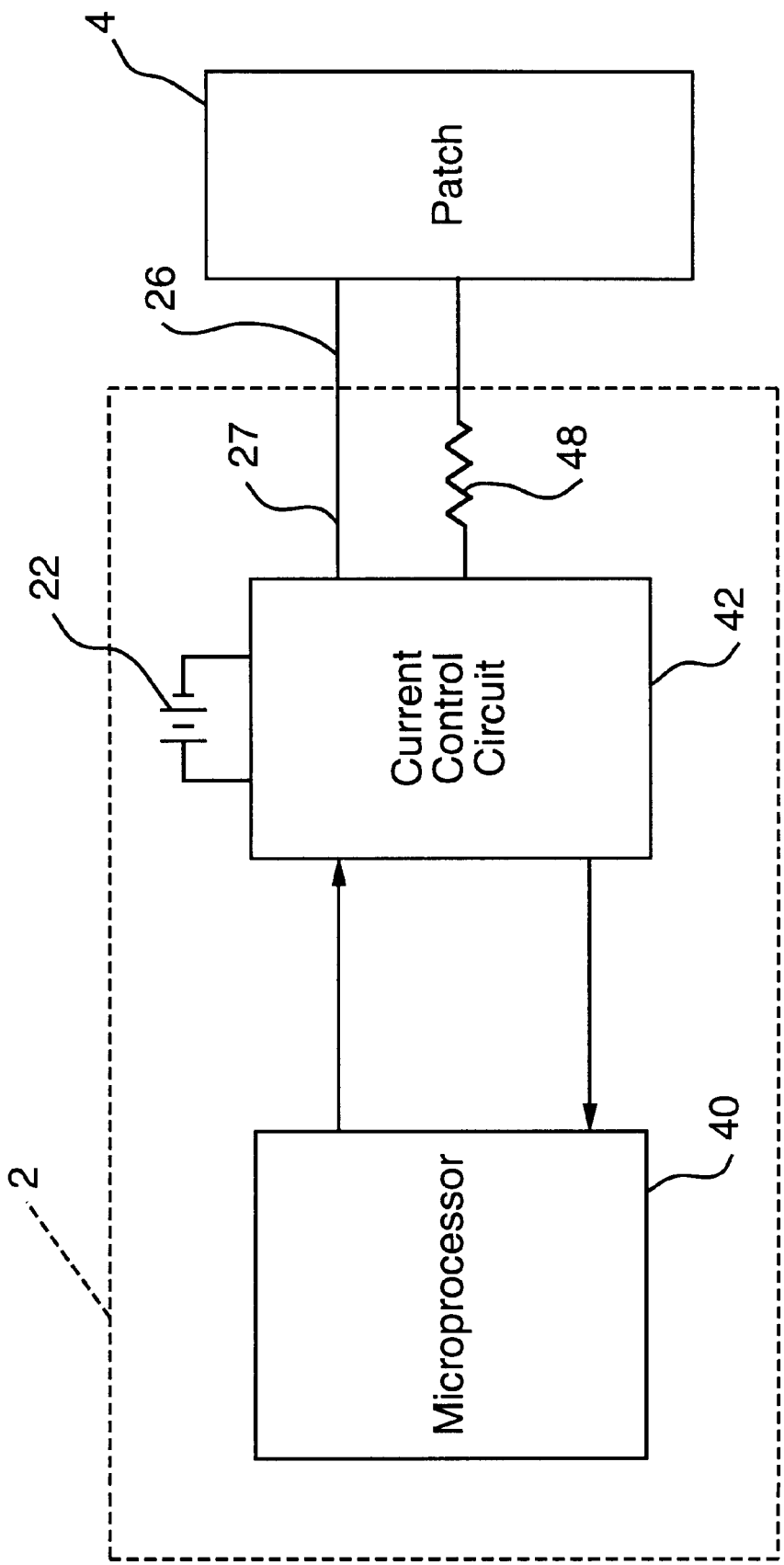
FIG. 3 is a block diagram of a iontophoretic controller circuit.

The controller 2 may include, but is not limited to, battery 22, microprocessor 40, and current control circuit 42, as shown in FIG. 3. The microprocessor 40 provides signals to the current control circuit 42 to ensure that the required current is delivered by the current control circuit 42 to the connected patch through conductors 27 and 26 to electrodes 8 and 10 (shown in FIG. 2) so that the correct amount of drug is delivered to the patient. The current control circuit 42 will produce from the battery 22 the required output current irrespective of the varying resistance and/or capacitance of the load (including the patient's skin, the impedance of which normally varies from patient to patient and which may change as iontophoresis takes place).

Further, voltage from a sensor, such as a current sense resistor 48, is monitored by the current control circuit 42 to ensure that the amount of delivered current is constant. The current passing through the current sense resistor 48 is the amount of current actually being delivered through the iontophoretic patch and skin. If less or more than the required current is being delivered, as indicated by the current sense resistor 48, the current control circuit 42 will adjust the current to the required level.

In order to increase the safety of the iontophoretic drug delivery system, it would be advantageous to stop the delivery of drugs to the patient when the supply voltage drops below a predetermined threshold. This would prevent improper operation of the current delivery circuitry due to the applied supply voltage being less than the value for which the circuit was designed.

Figure 4:
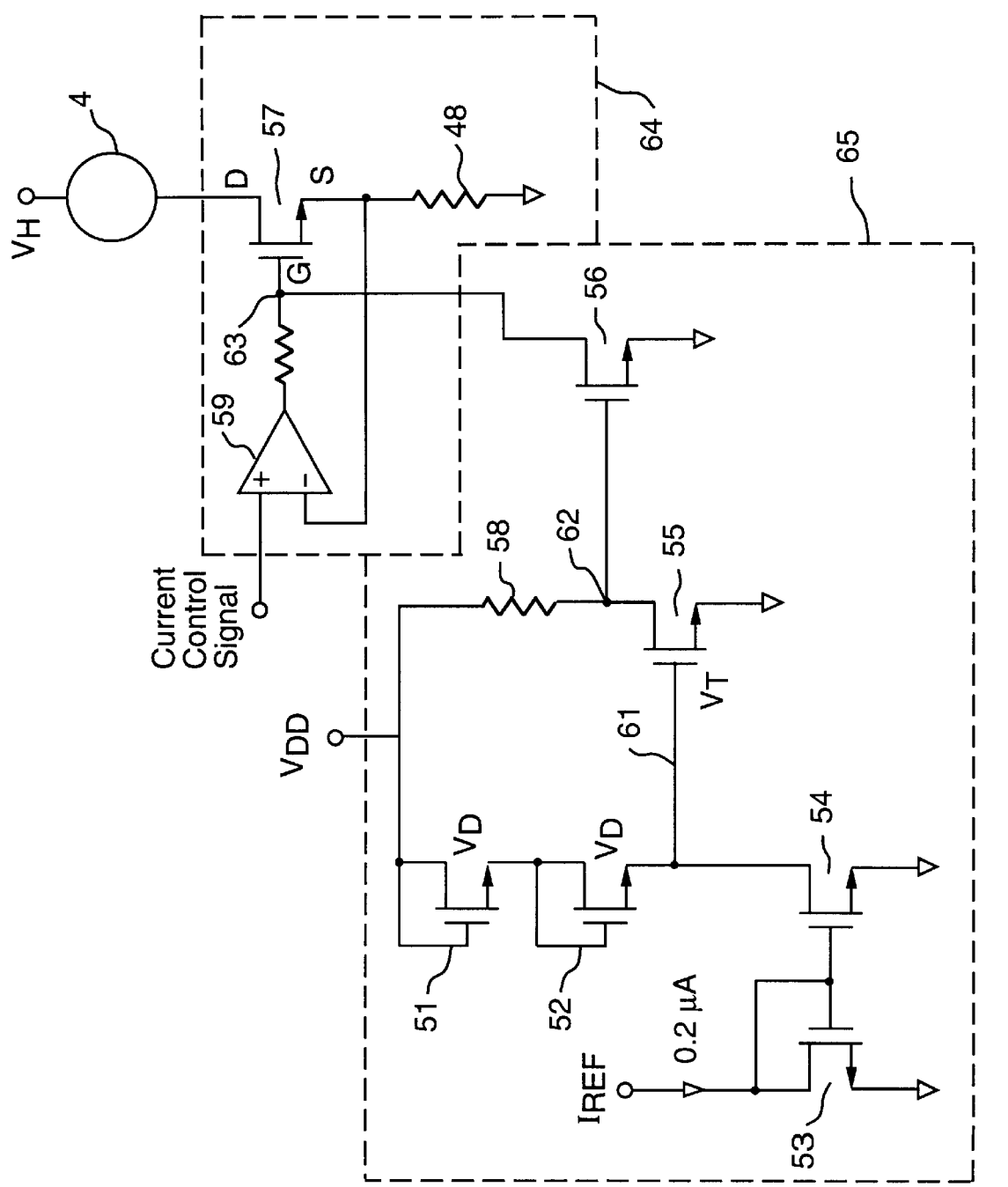
FIG. 4 is schematic diagram of a current control circuit with a low supply voltage disabling feature, in accordance with a first embodiment of the present invention.

FIG. 4 is a circuit diagram of a preferred embodiment of the present invention that shuts down the current supplied to patch 4 when the supply voltage gets too low. The circuit includes a current control circuit, depicted in the box 64, for controlling the current that flows through an iontophoretic patch. The circuit also includes a voltage detection circuit, depicted in the box 65, for shutting down the current control circuit when the supply voltage falls below a predetermined threshold.

The current control circuit includes the operational amplifier (op amp) 59, a transistor 57, and a current sense resistor 48. The current control circuit can only control current to the patch 4 when transistor 56 is off. Accordingly, the operation of the current control circuit will be explained below assuming that the transistor 56 is off.

The current control circuit uses negative feedback to control the desired amount of current that is to pass through the patch 4. The magnitude of the desired current is set by a current control signal which is supplied from another part of the controller (not shown).

The current control signal is input to the non-inverting input of the op amp 59. The current control signal varies from zero volts to a maximum positive voltage. When the control signal is sufficiently positive, it will cause the output voltage of the op amp 59 to rise, which will turn on the transistor 57. When the transistor 57 turns on, current flows through the patch 4, the transistor 57, and the current sense resistor 48. This current results in a voltage $V_{R48}$ across the current sense resistor 48. This voltage $V_{R48}$ is fed back to the inverting input of the op amp 59, to provide negative feedback. As long as the voltage at the inverting input is lower than the current control signal voltage at the non-inverting input, the output voltage of the op amp 59 will continue to rise. This will increasingly turn on the transistor 57 thereby increasing the current flowing through the patch and the current sense resistor 48.

When the current flowing through the current sense resistor 48 is high enough to result in a voltage across that resistor that is equal to the control signal, the output of the op amp 59 will stabilize. The current at which the op amp output stabilizes can be computed using Ohm's law, and is equal to the current control signal voltage divided by the resistance of the current sense resistor 48. If the output current ever become too high, negative feedback will reduce the output current to the desired value.

This current control circuit is disabled by preventing the transistor 57 from turning on, because when the transistor 57 is off, no current flows through the patch.

A preferred approach to preventing the transistor 57 from turning on is by grounding the node 63, which is the gate of the transistor 57. This keeps the gate to source voltage, $V_{GS}$, below the turn-on threshold of the transistor 57, so that the transistor 57 does not turn on.

The voltage detection circuit has an output that can ground the gate of the transistor 57, and thereby turn off the current control circuit as described above. The operation of this voltage detection circuit will now be described.

The voltage detection circuit includes a current mirror circuit, a voltage reference, and an output stage. The transistors 53 and 54 are arranged as a current mirror. A reference current is supplied to the $I_{REF}$ reference input of the current mirror. This reference current is preferably between 0.1 and 100 μA, and most preferably 0.2 μA. The current mirror ensures that this same current also flows through the transistor 54.

The same current also flows through the transistors 51 and 52 because they are connected in series with the transistor 54. The transistor 51 and the transistor 52 are each arranged with their gate connected to their drain. In this configuration, the transistors 51 and 52 act as diodes. When current flows through the transistors 51 and 52, a voltage drop $V_D$ will appear across each of the transistors 51 and 52. Therefore, because the drain voltage of the transistor 51 is $V_{DD}$, the voltage at the source of the transistor 51 will be $V_{DD}-V_D$, and the voltage at the node 61 will be $V_{DD}-2V_D$.

When the voltage at the node 61 is greater than the gate-to-source turn-on voltage of the transistor 55, the transistor 55 will turn on. Thus, if the turn-on voltage of the transistor 55 is $V_T$, the transistor 55 will turn on when $V_{DD}-2V_D \geq V_T$. Rearranging this equation, it is apparent that the transistor 55 will turn on only when $V_{DD} \geq V_T+2V_D$.

When the supply voltage $V_{DD}$ is greater than or equal to $V_T+2V_D$, transistor 55 turns on, which grounds the node 62. When the node 62 is grounded, the transistor 56 will be off, and node 63 will not be shorted to ground. This will allow the current control circuit to operate normally, as described previously.

On the other hand, when the supply voltage $V_{DD}$ is less than $V_T+2V_D$, the transistor 55 will be off. In this condition, there will be virtually no current flowing through the pull-up resistor 58 (preferably 2.2 MΩ), and the voltage at both terminals of the pull-up resistor 58 will be essentially the same. When this occurs, the power supply voltage $V_{DD}$ appears at the node 62, which is the gate of the transistor 56. This turns on the transistor 56, which shorts the node 63 to ground. Because the node 63 is connected to the gate of the transistor 57, the gate-to-source voltage $V_{GS}$ of the transistor 57 can not rise to the turn-on voltage of the transistor 57, which keeps the transistor 57 turned off so that no current flows through to the patch 4.

This circuit is designed to operate properly even when the supply voltage is extremely low. Because both the transistors 57 and 56 are preferably manufactured on the same substrate and matched to have similar characteristics, they would ordinarily turn on at the same gate-to-source voltage $V_{GS}$. But the circuit ensures that, when the supply voltage is low, but still high enough to turn on a transistor, the transistor 56 will turn on before the transistor 57, thereby preventing the current from flowing to the patch 4.

In the circuit, because the source of the transistor 56 is grounded, the transistor 56 can turn on as soon as the voltage at the node 62, which is the gate of the transistor 56, rises to the $V_{GS(TURN-ON)}$. In contrast, because the voltage at the source of the transistor 57 is raised above ground by the voltage across the resistor 48 ($V_{R48}$), the transistor 57 can not turn on until the voltage at the node 63, which is the gate of the transistor 57, rises to $V_{GS(TURN-ON)}+V_{R48}$. Because the transistor 57 will not turn on until the voltage at the node 63 is $V_{GS(TURN-ON)}+V_{R48}$, and the transistor 56 will turn on when the voltage at the node 62 is $V_{GS(TURN-ON)}$, the transistor 56 will always turn on before the transistor 57 when the supply voltage is low. This will short the node 63 to ground, which keeps the transistor 57 turned off, thereby preventing any current supply to the patch 4.

Of course, it will be appreciated that the invention may take forms other than those specifically described. For example, the op amp may be used as an inverting amplifier instead of a non-inverting amplifier, or bipolar junction transistors may be used in place of field effect transistors. Alternatively, the current control signal may be a bipolar signal or a negative signal. These and numerous other variations are well known to those skilled in the art of analog circuit design. The scope of the invention is to be determined solely by the following claims.

What is claimed is:

1. A fail-safe iontophoretic apparatus, comprising:
   a voltage detection circuit having an output that is asserted when a supply voltage falls below a predetermined level; and
   a current control circuit having an output transistor through which an iontophoretic output current passes, the output transistor having a control input,
   wherein the voltage detection circuit output, when asserted, drives the control input of the output transistor to a level that prevents the output transistor from turning on, stopping the iontophoretic output current.

2. The apparatus according to claim 1, further comprising an iontophoretic patch.

3. The apparatus according to claim 1, wherein the output transistor is a field effect transistor having a gate, and the control input is the gate.

4. The apparatus according to claim 1, wherein the level that prevents the output transistor from turning on is approximately ground.

5. The apparatus according to claim 1, further comprising a current sense resistor connected in series with a path of the output current.

6. The apparatus according to claim 1, further comprising an operational amplifier having an output connected to drive the control input of the output transistor, wherein a signal related to output current is fed back to an inverting input of said operational amplifier.

7. The apparatus according to claim 1, wherein the iontophoretic current control circuit includes:

a current sense resistor connected in series with a path of the output current; and an operational amplifier having an output connected to drive the control input of the output transistor, and wherein a voltage induced across the resistor is fed back to an inverting input of the operational amplifier.

8. The apparatus according to claim 7, wherein the output transistor is a field effect transistor having a gate, the control input is the gate, and the level that prevents the output transistor from turning on is approximately ground.

9. The apparatus according to claim 8, further comprising an iontophoretic patch.

10. The apparatus according to claim 1, wherein the voltage detection circuit includes:

a current mirror having a reference input and an output node;

a voltage-dropping element connected between the supply voltage and the current mirror output node;

a first transistor having a gate, a grounded source, and a drain, the first transistor's gate connected to the current mirror output node;

a resistor connected between the supply voltage and the first transistor's drain; and a second transistor having a gate, a grounded source, and a drain, the second transistor's gate connected to the first transistor's drain, and the second transistor's drain connected to the voltage detection circuit output.

11. The apparatus according to claim 10, wherein the voltage-dropping element comprises a third transistor having a drain connected to a gate, and a fourth transistor having a drain connected to a gate, and wherein the source of the third transistor is connected to the gate of the fourth transistor.

12. The apparatus according to claim 10, wherein the current mirror output current is approximately 0.2 $\mu A$.

13. The apparatus according to claim 10, wherein the current mirror output current is between approximately 0.1 $\mu A$ and approximately 100 $\mu A$.

* * * * *